United States Patent [19]
Rosen et al.

[11] Patent Number: 5,129,396
[45] Date of Patent: Jul. 14, 1992

[54] MICROWAVE AIDED BALLOON ANGIOPLASTY WITH LUMEN MEASUREMENT

[76] Inventors: Arye Rosen, 508 Heartwood Rd., Cherry Hill, N.J. 08003; Paul Walinsky, 220 E. Mermaid La., Townhouse #218, Philadelphia, Pa. 19118

[21] Appl. No.: 584,062
[22] Filed: Sep. 18, 1990

Related U.S. Application Data

[62] Division of Ser. No. 269,960, Nov. 10, 1988, abandoned.

[51] Int. Cl.$^5$ ................................................ A61B 5/00
[52] U.S. Cl. .................................. 128/653.1; 128/804
[58] Field of Search .................. 128/653 R, 668, 713, 128/784, 786, 804, 774

[56] References Cited

U.S. PATENT DOCUMENTS

| | | |
|---|---|---|
| 3,605,046 | 9/1971 | Miller . |
| 3,661,148 | 5/1972 | Kolin ........................... 128/774 |
| 4,328,811 | 5/1982 | Fogarty ........................ 128/774 |
| 4,583,556 | 4/1986 | Hines et al. . |
| 4,612,940 | 9/1986 | Kasevich et al. . |
| 4,641,649 | 2/1987 | Walinsky et al. . |
| 4,643,186 | 2/1987 | Rosen et al. ................. 128/804 |
| 4,662,383 | 5/1987 | Sogawa et al. . |
| 4,692,864 | 9/1987 | Shimoni et al. . |
| 4,700,716 | 10/1987 | Kasevich et al. ............ 128/804 |
| 4,739,276 | 4/1988 | Graube . |
| 4,743,230 | 5/1988 | Nordquest . |
| 4,743,753 | 5/1988 | Cheng et al. . |
| 4,754,752 | 7/1988 | Ginsburg et al. . |
| 4,762,129 | 8/1988 | Bonzel . |
| 4,770,653 | 9/1988 | Shturman . |
| 4,773,899 | 9/1988 | Spears . |
| 4,799,479 | 1/1989 | Spears . |
| 4,807,620 | 2/1989 | Strul et al. . |
| 4,808,164 | 2/1989 | Hess ............................ 128/804 |
| 4,825,880 | 5/1989 | Stauffer et al. . |

OTHER PUBLICATIONS

"Vector System Tackles MM-Wave Measurements", by Pervere, published at page 185 of Microwaves & RF Magazine, Jan. 1988.

*Primary Examiner*—Ruth S. Smith
*Attorney, Agent, or Firm*—William H. Meise

[57] ABSTRACT

A multipurpose catheter apparatus for microwave aided balloon angioplasty includes a balloon capable of being filled with a lossy dielectric liquid, and bearing a metallization pattern. The catheter includes an electromagnetic transmission line. Radio frequency energy applied to the proximal end of the electromagnetic transmission line is radiated by an antenna within the balloon. The metallization pattern causes a portion of the energy applied to the proximal end of the transmission line to be reflected, which affects a characteristic such as impedance, return loss or time of reflection. A measurement apparatus measures the characteristic, and the distention of the balloon is determined from the measured characteristic. A guide filament may extend through the transmission line.

11 Claims, 10 Drawing Sheets

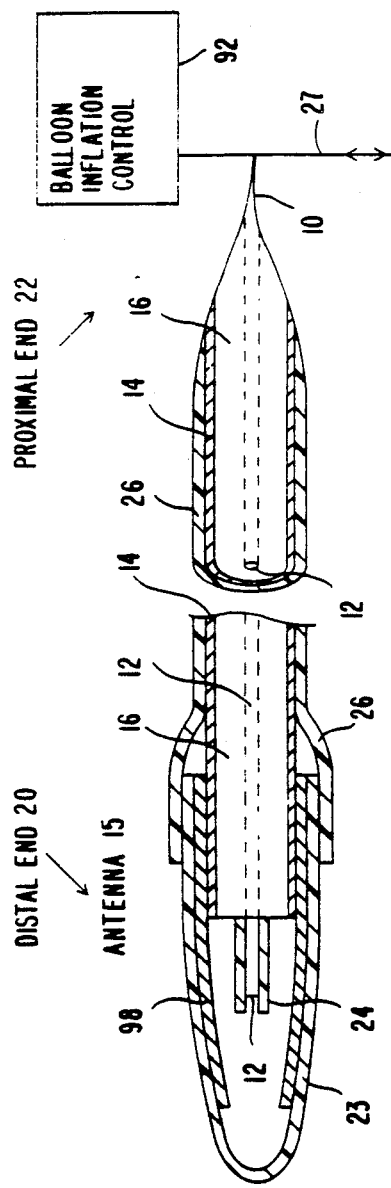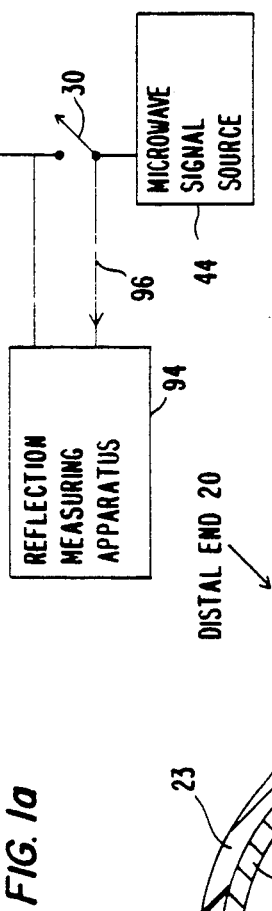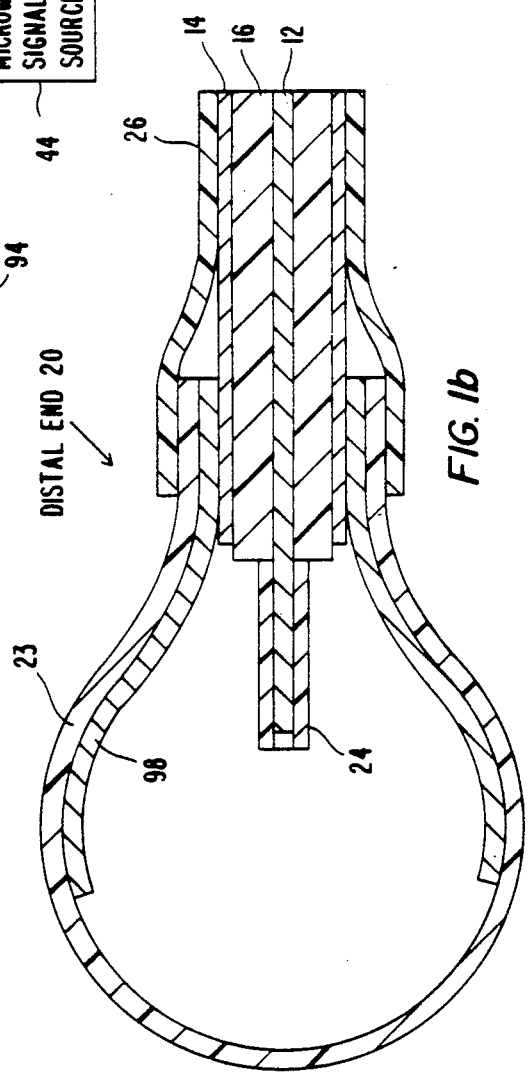

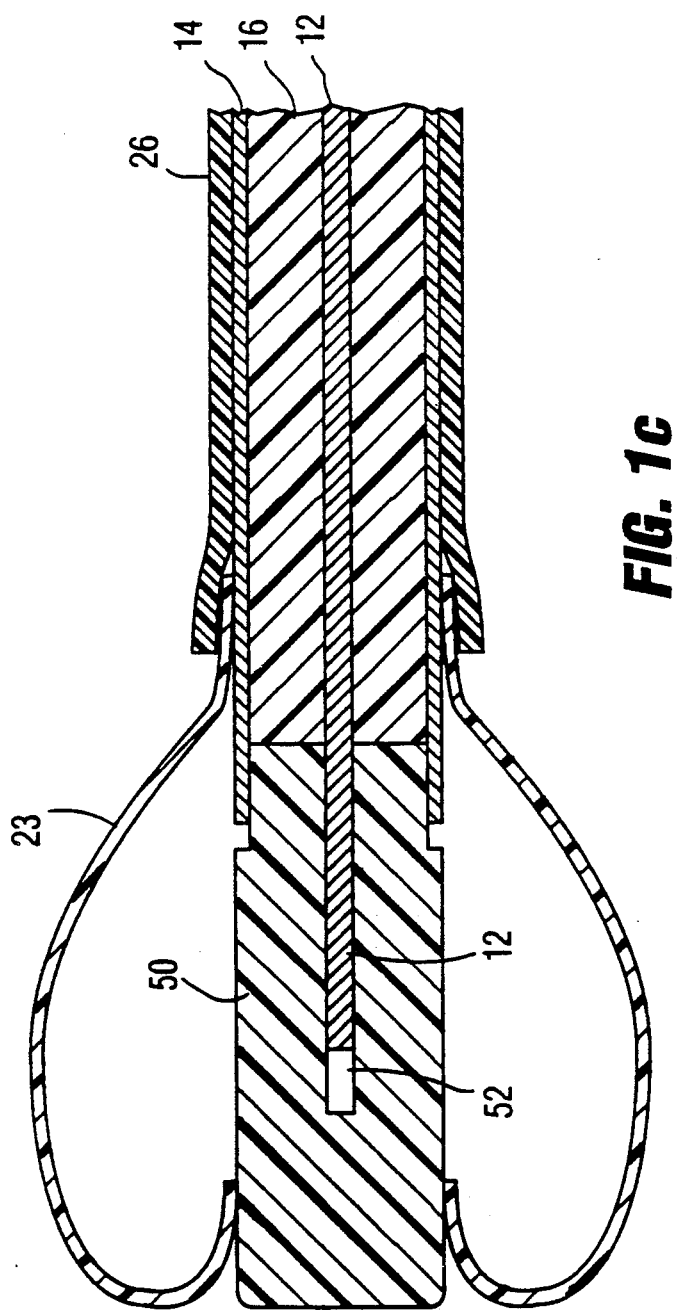

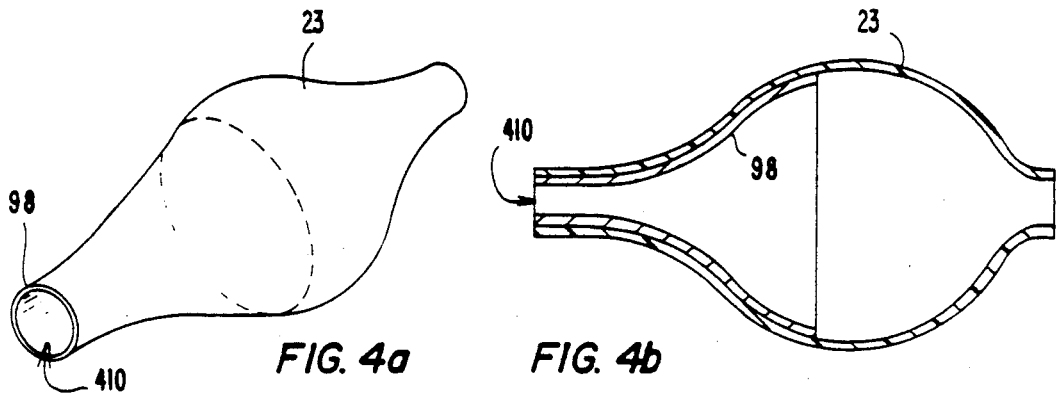
FIG. 4a  FIG. 4b
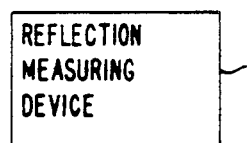
FIG. 5a  FIG. 5b
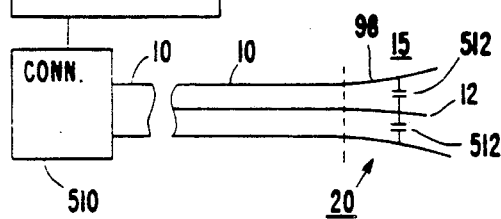
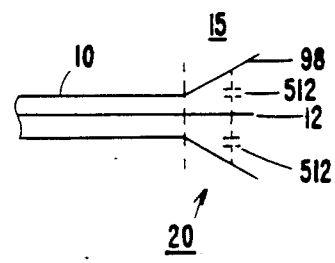
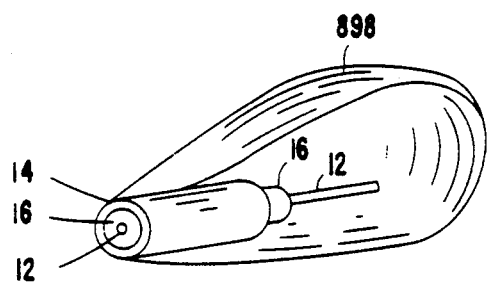
FIG. 8
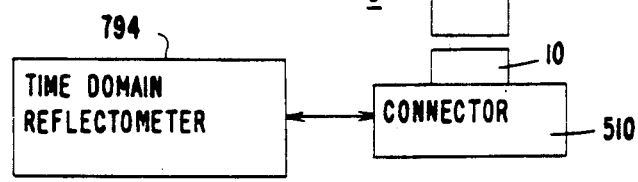
FIG. 7

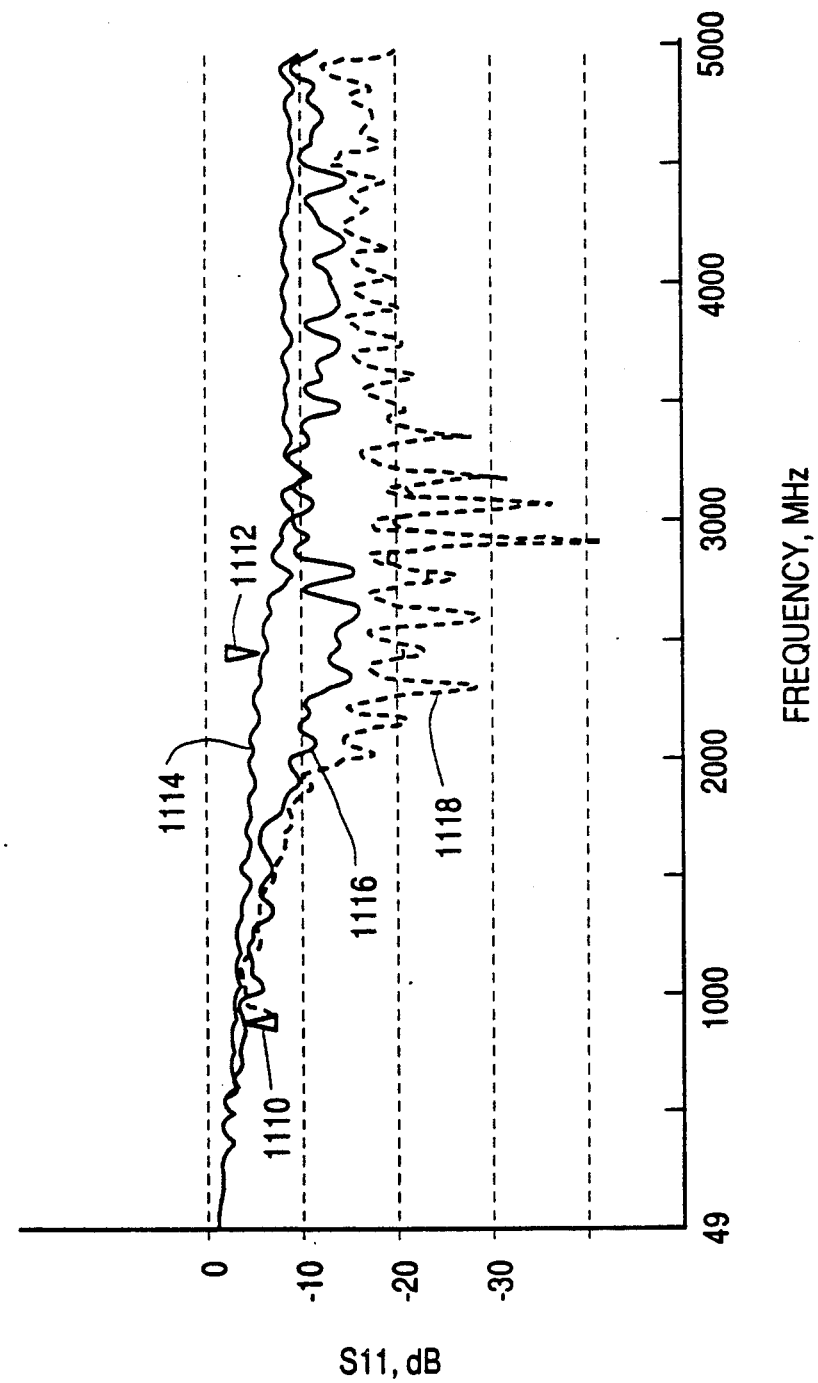

MICROWAVE AIDED BALLOON ANGIOPLASTY WITH LUMEN MEASUREMENT

This is a division of U.S. Patent application Ser. No. 07/269,960 filed Nov. 10,1988 now abandoned.

This invention relates to microwave aided balloon catheter angioplasty in which the catheter includes a coaxial transmission line, with which a guide filament may be used.

BACKGROUND OF THE INVENTION

Several hundred thousand people die suddenly in the United States each year from acute myocardial infarction, and many more suffer from chronic heart problems. A major contributing factor in both acute and chronic heart problems is a reduction in nutrient blood flow to the muscles of the heart resulting from a reduction of blood flow through the coronary blood vessels. The reduction in flow may be caused by deposits of atherosclerotic plaque on the walls of the blood vessel, which causes a narrowing of the lumen or channel of the blood vessel. When the lumen is sufficiently narrowed, the rate of flow of blood may be so diminished that spontaneous formation of a thrombus or clot occurs by a variety of physiologic mechanisms. As is known, once a blood clot has started to develop, it extends within minutes into the surrounding blood, in part because the proteolytic action of thrombin acts on prothrombin normally present, tending to split this into additional thrombin which causes additional clotting. Thus, the presence of atherosclerotic plaque not only reduces the blood flow to the heart muscle which it nourishes, but is a major predisposing factor in coronary thrombosis.

Among the treatments available for the conditions resulting from plaque formations are pharmacological means such as the use of drugs, for example nitroglycerin, for dilating the coronary blood vessels to improve flow. In surgical treatment may be indicated. One of the surgical techniques commonly used is the coronary bypass, in which a substitute blood vessel shunts or bypasses blood around the blockage. The bypass operation is effective but is expensive and subject to substantial risks.

Percutaneous transluminal balloon catheter angioplasty is an alternative form of treatment. This method involves insertion of a deflated balloon into the lumen of an artery partially obstructed by plaque, and inflation of the balloon in order to enlarge the lumen. The lumen remains expanded after removal of the catheter. The major problem with this technique is restenosis of the narrowed vessel by recurrence of the arterial plaque.

Another technique which has recently received a good deal of attention is transluminal laser catheter angioplasty. This treatment involves introduction into the coronary artery of a fiber optic cable the proximal end of which is connected to a laser energy source. The distal end of the fiber optic cable is directed towards the plaque. The laser is pulsed, and the resulting high energy light pulse vaporizes a portion of the plaque. Many problems remain unsolved in laser catheter angioplasty. Locating the plaque requires some means such as a fiber optic scope to see the region towards which the laser pulse will be directed. The interior of the artery must be illuminated, and a clear liquid introduced into the artery to displace opaque blood from the region to be viewed. Even with a fiber optic scope, however, the plaque may be difficult to distinguish from normal arterial walls. When the energy of the laser discharge is directed towards the arterial walls, the walls may undesirably be perforated. Further problems relate to the difficulty in matching the characteristic of lasers and fiber optic cables to the frequency absorption characteristics of various types of plaque, and the by-products of the destruction of the plaque.

Microwave aided balloon angioplasty is described in U.S. Pat. No. 4,643,186 issued Feb. 17, 1987 in the name of Rosen et al. In the arrangement as described by Rosen et al., a catheter including a microwave transmission line terminates at its distal end in an antenna. The antenna is surrounded by a balloon. During angioplasty, the catheter is introduced into a blood vessel or other vas, and the distal end with the balloon and the antenna is manipulated to a point adjacent the plaque. Microwave power is applied to the proximal end of the catheter and flows to the antenna, which radiates the energy to the plaque for heating and thereby softening the plaque. The balloon is expanded against the softened plaque to thereby expand the lumen of the blood vessel. It would be desirable to be able to determine the expanded size of the balloon to thereby determine the diameter to which the lumen of the blood vessel has been expanded. It would be desirable to be able to guide the catheter with a filament. It would be desirable to be able to heat adjacent tissue both conductively and by radiation absorption.

SUMMARY OF THE INVENTION

A microwave aided catheter which may be useful for balloon angioplasty and for other purposes includes a coaxial transmission line with center and outer conductors and a dielectric sheath therebetween. According to an aspect of the invention, The center conductor of the transmission line is hollow, and permits axial movement therethrough of a guide wire or filament. In one embodiment of the invention, the transmission line terminates in an antenna for radiating microwaves. A balloon surrounds the antenna in another embodiment of the invention.

DESCRIPTION OF THE DRAWING

FIG. 1a is a cross-section of a catheter according to the invention, illustrating in simplified form connections at the proximal end to a source of power and to a lumen diameter measuring arrangement, FIG. 1b is a cross-section of the distal end of the catheter of FIG. 1a, illustrating details of the construction, and FIG. 1c is a cross-section of an alternative balloon construction, FIGS. 1a, 1b and 1c are together referred to as FIG. 1;

FIG. 4a illustrates in perspective view a partially expanded balloon illustrating a metallization pattern on the interior of the balloon, and FIG. 4b is a cross-section thereof, FIGS. 4a and 4b are jointly referred to as FIG. 4;

FIG. 5a illustrates in simplified form the capacitance between the antenna and balloon metallization with a slightly inflated balloon, and FIG. 5b illustrates the reduced capacitance of a more inflated balloon;

FIG. 7 illustrates the path length differences of the reflected signal attributable to balloon inflation condition;

FIG. 8 is a perspective view of a metallization pattern which directs energy laterally;

FIGS. 10a and 10b are together referred to as FIG. 10;

FIG. 11 is a tracing of plots made by an automatic plotter of the $S_{11}$ characteristic of a coaxial cable terminated in an antenna surrounded by a saline-filled metallized balloon at various inflations;

DESCRIPTION OF THE INVENTION

Figure 2:
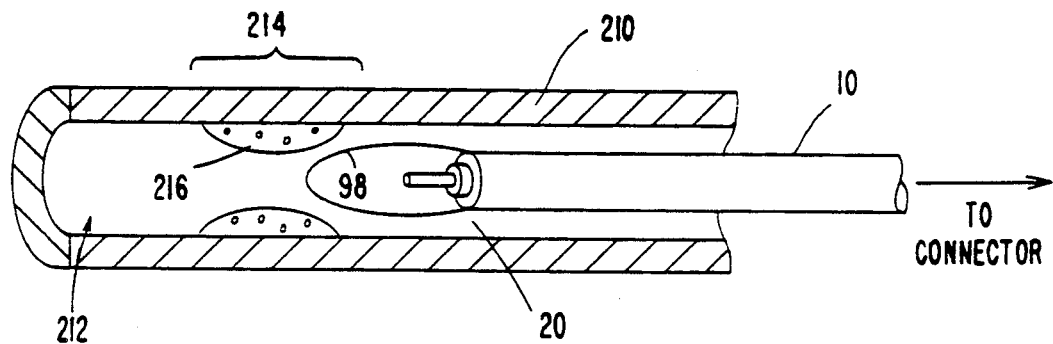
FIG. 2 is a perspective view, partially cut away, of a catheter according to the invention within a blood vessel, which is partially occluded by plaque.

In FIG. 1a, a flexible catheter designated generally as 8 includes a flexible coaxial transmission line (coax) 10 including a flexible center conductor 12 coaxial with a flexible cylindrical outer conductor or sheath 14. An insulating or dielectric material 16 fills the space between center conductor 12 and outer conductor 14 for holding center conductor 12 and outer conductor 14 in place and for electrically isolating the conductors from each other. Flexible conductive sheath or braid 14 is surrounded over most of its length by flexible jacket 26 made of a relatively impermeable material such as polyvinylchloride (PVC). A suitable type of coaxial transmission line is type CZ1174 or type AS450-3650F having nominal outer diameters of 0.024 and 0.019 inches, respectively. This cable is made specifically for biomedical use by Cooner Wire Company, 9186 Independence Avenue, Chatsworth, CA 91311. The strands of the center and outer conductors may be silver-soldered or brazed together at their distal ends to maintain structural integrity. At the distal end 20 of catheter 8 dielectric material 16 extends somewhat past the distal end of outer conductor 14, and center conductor 12 extends past the end of dielectric material 16. A small sheath or tube of dielectric material 24 covers that portion of center conductor 12 which extends beyond the distal end of dielectric material 16.

In the alternative arrangement of FIG. 1C, a larger sheath of dielectric material 50 accepts the distal end of center conductor 12 in a bore 52.

As is well known in the antenna arts, such an arrangement constitutes an antenna designated generally as 15 which when receiving radio frequency (RF) electrical energy from the proximal end 22 of coaxial cable 10 radiates electromagnetic energy away from the distal end 20 of catheter 8. At its proximal end 22, coax 10 of catheter 8 is coupled by way of standard mating connectors (not illustrated in FIG. 1a) through a further coaxial transmission line 27 to a switch illustrated by a mechanical switch symbol 30. Those skilled in the art know that a system of double-pole, double throw transmission-line switches should be used. When switch 30 is closed, the proximal end 22 of coaxial cable 10 is connected to a microwave frequency signal source 44. As known in the art, microwave frequency signal source 44 may include frequency meters, power meters and attenuators for adjusting the amount of power applied by way of switch 30 and coaxial cable 27 to the proximal end 22 of coaxial cable 10. At distal end 20 of catheter 8, the protruding tip of center conductor 12 is surrounded by a balloon defined by a dielectric membrane 23. While illustrated as having substantial thickness, the membrane is actually thin. A portion of the inside surface of membrane 23 is covered with a metallization layer illustrated as 98.

Balloon membrane 23 together with its metallization coating 98 defines an os or mouth which fits snugly about a portion of the distal end of conductive sheath 14. PVC jacket 26 at its distal end fits over the outer surface of the os of balloon membrane 23 in a sealing manner. With this arrangement, metallization 98 is in intimate contact with conductive sheath 14. No solder or metallurgical contact is necessary, because even in the absence of a full metallurgic contact, the capacitance between metallization coating 98 and metallic conductive sheath 14 provides good coupling at microwave frequencies. Dielectric sheath 24 is provided to prevent contact between metallization layer 98 and the distal end of center conductor 12. Dielectric piece 50 is provided to additionally provide support to a second os at the distal end of the balloon in the alternative arrangement of FIG. 1C.

A balloon inflation control arrangement 92 is connected to proximal end 22 of coax 10. Connection may be made between inflation control 92 and transmission line 27 with proximal end of coax cable 10 by means of a connector such as that illustrated in the aforementioned Rosen et al. patent.

With switch 30 in the illustrated open state, microwave signal source 44 is coupled by way of a transmission line 96 to a microwave frequency reflection measuring apparatus, which is coupled by way of transmission line 27 to the proximal end of coaxial cable 10. As known to those skilled in the art, reflection measuring apparatus 94 allows measurement of the magnitude or phase, or both, of the energy reflected from catheter 8 into the measuring apparatus relative to the energy exiting therefrom. In accordance with an aspect of the invention, the radius or the amount of inflation of balloon membrane 23 is determined, in one mode of operation, by applying microwave signal by way of reflection measuring apparatus 94, cable 27 and coax 10 to antenna 15 at the distal end 20 of catheter 8. A parameter of the signal reflected from antenna 15 back through coaxial cable 10 and cable 27 to the reflection measuring apparatus makes it possible to determine the amount of inflation.

Figure 3A:
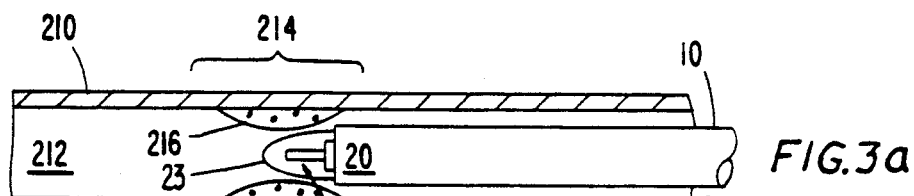
FIGS. 3a, 3b, 3c and 3d, referred to jointly as FIG. 3, illustrate various conditions of the catheter of FIGS. 1 and 2 during microwave aided balloon angioplasty in accordance with the invention.
Figure 3B:
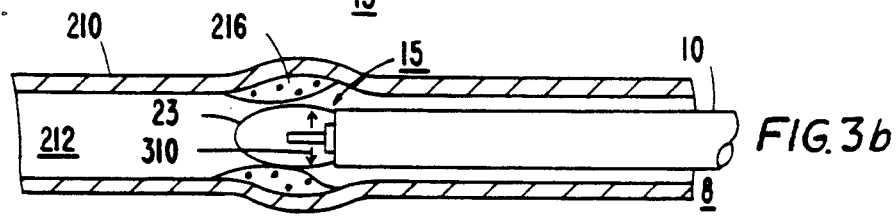

FIG. 2 illustrates in cut-away view a stenotic (narrow) artery in which the muscle wall is designated 210, defining a lumen 212. A region 214 defines a stenotic region in which the lumen is partially occluded by atherosclerotic plaque. The distal end 20 of catheter 8 including a portion of coax 10, antenna 15 and balloon membrane 23 is inserted transluminally. The position of antenna 15, as illustrated, is near stenotic plaque 216. In accordance with an aspect of the invention, microwave aided catheter angioplasty includes steps illustrated in FIG. 3. FIG. 3a illustrates the insertion of a catheter 8 including coaxial cable 10 transluminally, and the placement of distal end 20 adjacent region 214 in which plaque 216 occurs. FIG. 3b illustrates the partial inflation of balloon membrane 23 against the resistance of the plaque while irradiating the plaque with microwave energy represented by arrows 310.

Figure 3C:
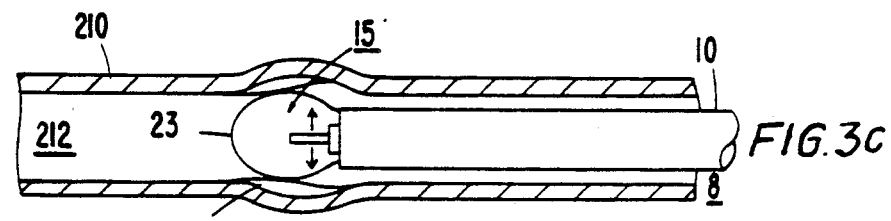
Figure 3D:
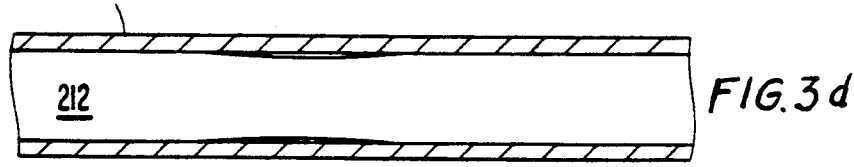

FIG. 3b also illustrates the measurement of the radius of the balloon by measurement of a parameter of the microwave signal reflected from antenna 15. In the case of FIG. 3b, the expansion of the balloon is not great, indicating that further angioplasty is required. FIG. 3c illustrates a further inflation of balloon membrane 23 against the resistance of plaque 216 together with application of additional microwave energy, either at the same power level or possibly at a higher power level. The power softens the plaque, reducing the resistance to balloon expansion. The additional inflation of balloon membrane 23 further compresses plaque 216 to cause lumen 212 to be further opened. FIG. 3c also illustrates the conditions during measurement of reflected energy to thereby indicate on reflection measuring apparatus 94 (FIG. 1a) that balloon membrane 23 has been inflated to an amount considered medically sufficient. FIG. 3d illustrates a condition in which the microwave power has been turned off, balloon membrane 23 deflated and catheter 8 removed.

FIG. 4a illustrates balloon membrane 23 in a perspective view looking from the side including mouth or os 410. FIG. 4b is a cross-sectional view of the balloon membrane 23 in the state illustrated in FIG. 4a. While the metallization is illustrated as extending into os 410, it should be noted that reflection of electromagnetic energy by metallization on the balloon surface does not depend upon a galvanic (direct) connection between the metallization and either center conductor 12 or outer conductor 14.

FIG. 5a is a simplified schematic representation of the connection of impedance reflection measuring device 94 coupled to an electrical and gas connector illustrated as a block 510, connected to coax 10. At distal end 20 of coaxial cable 10, protruding center conductor 12 has a capacitance to metallization 98 which is illustrated by capacitors 512. In FIG. 5b, balloon membrane 23 is inflated to a greater diameter than in FIG. 5a, and metallization 98 is at a greater distance from center conductor 12, and therefore a capacitance represented by capacitors 512 is smaller. The reduced capacitance of capacitors 512 is indicated in FIG. 5b by illustrating them in phantom. In the arrangement of FIG. 5, reflection measuring device 94 may be an impedance measuring device. As described below, the impedance is an indication of the physical relationship between the antenna 15 and the metallization on the balloon membrane.

FIG. 7 illustrates a connection of reflection measuring device 94 in a form of a time domain reflectometer by way of connector 510 and coax 10 to antenna 15 at the distal end 20 of catheter 8. Two positions are illustrated for the metallization supported by balloon membrane 23; a first position, illustrated in phantom as 598, is relatively close to center conductor 12. The second position, illustrated by solid lines 596, is more distant from center conductor 12 of antenna 15. Condition 596 of the metallization represents a more inflated condition of the associated balloon membrane.

As is known to those skilled in the art, the time domain reflectometer produces a pulse of energy including microwave components, which travels through the transmission line including transmission line 10 to antenna 12 and is radiated. A portion of the pulse is reflected, and is returned to the time domain reflectometer. The time interval between the initiation of the pulse by time domain reflectometer 94 and the time of the return of a reflection is displayed by the reflectometer. The reflectometer also displays a magnitude of the reflection, which is related to the impedance of the antenna. The reflectometer display is affected by the proximity of metallization to the antenna and may be calibrated to provide an indication of balloon diameter. At the present state of the art time domain reflectometry is less sensitive to distance than impedance measuring devices, so impedance measurements are preferred for small diameters such as coronary arteries.

Figure 9:
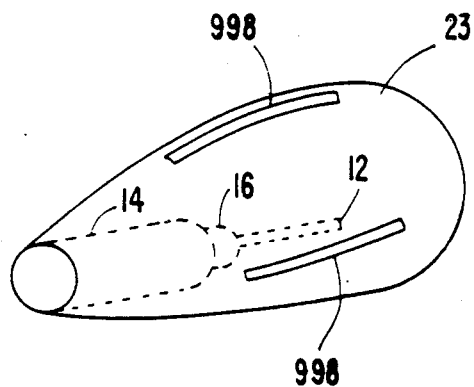
FIG. 9 is a perspective view of a balloon with a metallization pattern (which may be inside or outside) defining resonant or almost-resonant lengths.

As so far described, a balloon membrane 23 has been metallized with a simple reflector pattern. However, many other patterns are possible. FIG. 8 illustrates, without the supporting balloon membrane, a reflector 898 arranged for directing the radiated energy laterally of the longitudinal axis of catheter 8, rather than forwardly along the axis. Lateral distribution of energy may be preferred when the occluding plaque is partially occlusive and it is desired to heat a portion, but not the entire circumference of the vessel wall. FIG. 9 illustrates another useful pattern. In FIG. 9, balloon membrane 23 bears a number of longitudinal metallization stripes 998. Metallization stripes 998 are grouped on one side (the near side in FIG. 9) of balloon membrane 23, and each strip or stripe may have a length equal to or slightly greater than one wavelength at the operating frequency, if the dimensions of the balloon, and the dielectric constant of the fluid permit. As is known to those skilled in the art, such strips may act as reflectors, tending to reflect energy much as the solid reflector of FIG. 8. However, they are more frequency-sensitive than the solid or continuous reflector. If conductive metallization stripes 998 are somewhat less than one wavelength long in the deflated condition of the antenna, they have less of a tendency to reflect energy than when they are equal to or slightly greater than a wavelength in length. Consequently, as the balloon inflates the length of strips or stripes 958 increases, and the magnitude of the reflection from conductive metallization stripes 998 will tend to increase as their length approaches and exceeds resonance. This amplitude change may aid in determining the proper diameter of the balloon.

Figure 10A:
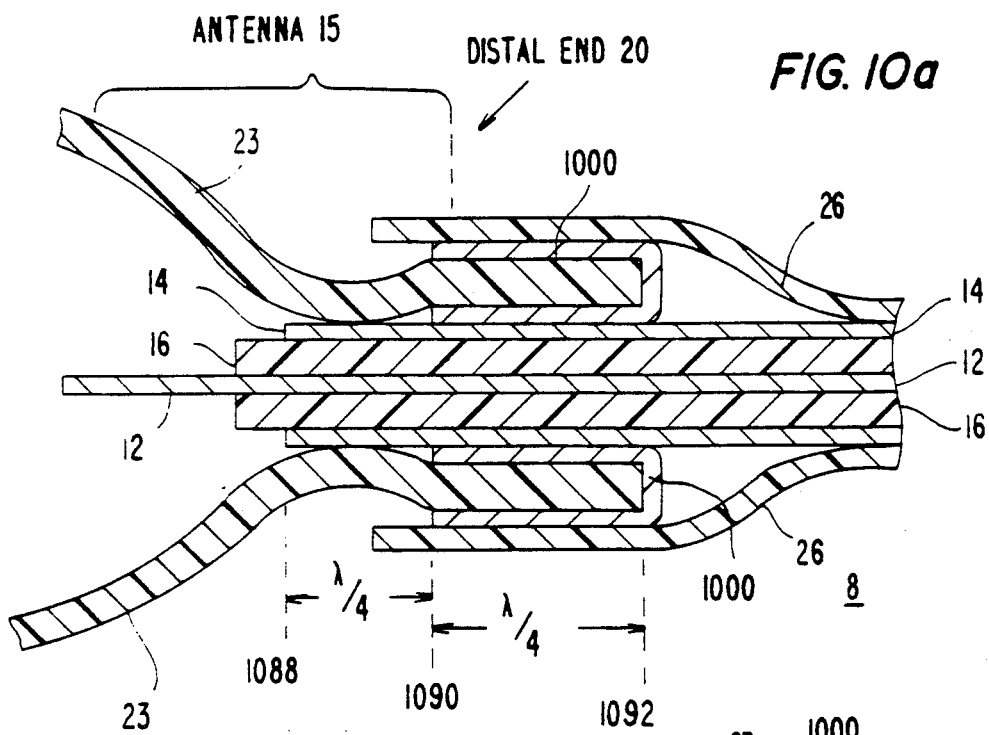
FIG. 10a is a cross-sectional view of the distal end of a catheter in which the balloon is metallized with a pattern defining a choke.
Figure 10B:
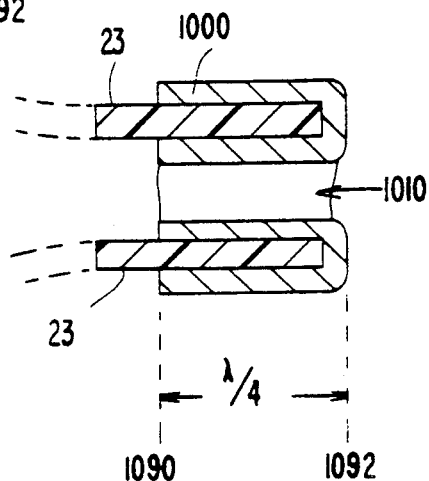
FIG. 10b is a cross-section of a portion of the balloon and the metallization alone.

FIGS. 10a, 10b illustrates an arrangement which aids in providing a more uniform and controlled radiation pattern. FIG. 10a is a cross-section of the distal end 20 of catheter 8. As illustrated in FIG. 10a, balloon membrane 23 is metallized with a pattern 1000, illustrated in more detail in FIG. 10b. In FIG. 10b, pattern 1000 can be seen to consist of annular metallized portions near the os 1010 of the balloon, joined together at the rear edge to form a roughly U shape in cross-section, with the U filled by balloon membrane. When the os of balloon 23 is fitted over conductive sheath 14 as illustrated in FIG. 10a, the interior portion of metallization pattern 1000 is in intimate contact with conductive sheath 14. As illustrated, the most distal end of metallization portion 1000 occurs at a transverse plane 1090, approximately one-quarter wavelength ($\lambda/4$) at the operating frequency from the distal end of conductive sheath 14, which occurs at a transverse plane 1088. Also, the length of the exterior portion of metallization 1000 measured axially is $\lambda/4$. Those skilled in the art will recognize the pattern of metallization 1000 as forming a quarter-wavelength choke, which presents a high impedance to the flow of current at transverse plane 1090, thereby restricting the radiating portion of antenna 15 to that portion extending from the tip of the protruding portion of center conductor 12 and that portion of conductive sheath 14 extending from plane 1088 to 1090. This is equivalent to a dipole, which has a well known radiation pattern.

Figure 6:
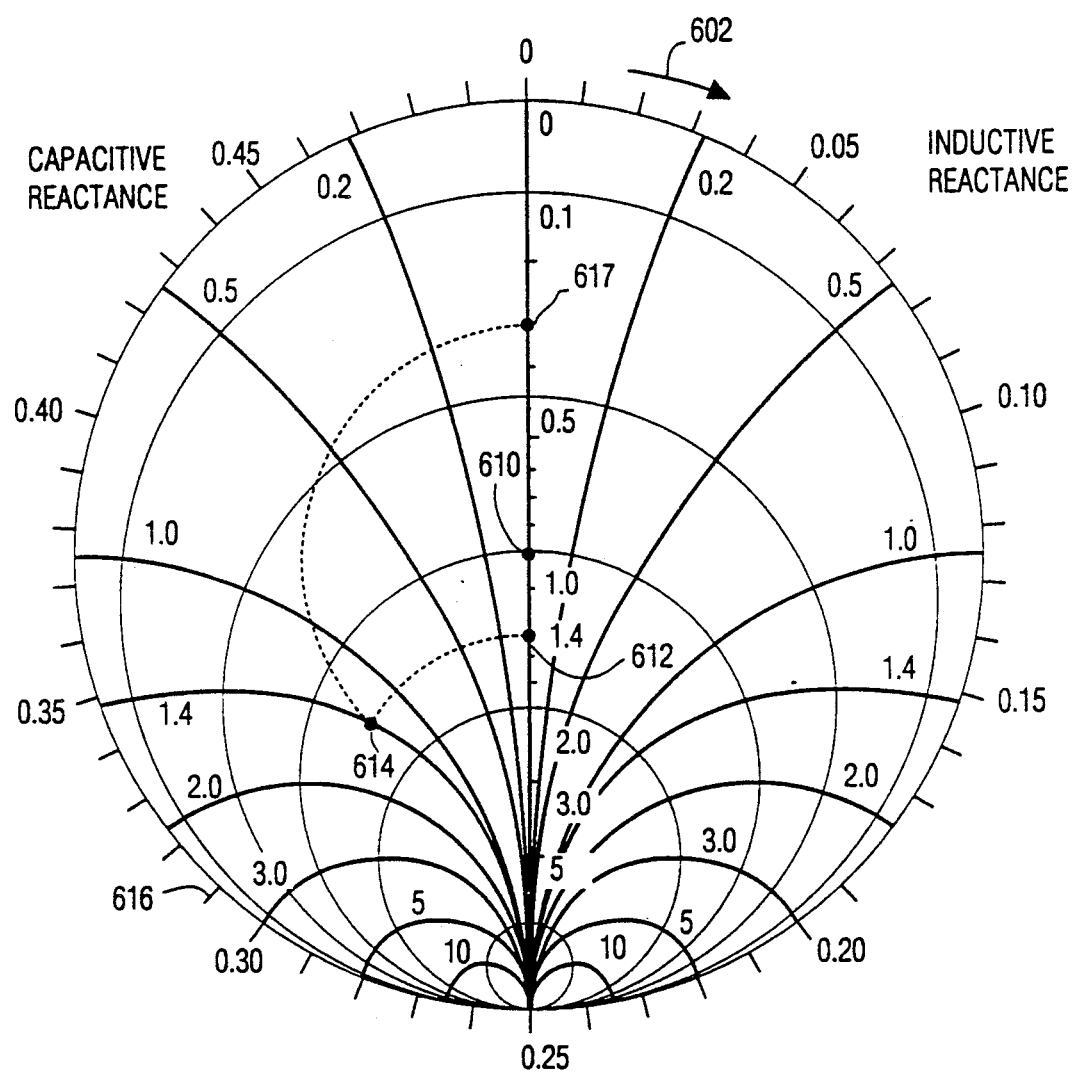
FIG. 6 illustrates a Smith chart for compensating for the effect of measuring at the proximal end of a long transmission line.

FIG. 6 illustrates a Smith chart representing all possible impedances. A Smith chart is useful for determining the phase of the impedance as viewed through a length of transmission line of normalized characteristic impedance equal to 1.0. For example, antenna 15 of FIG. 1 has an impedance at a given frequency which may include a reactive component as well as a resistance component. The apparent magnitude of the reactive component may appear to change if the impedance is viewed, as in FIG. 1a, at a distance from the impedance being measured. For example, in FIG. 1a, antenna 15 at the distal end 20 of catheter 8 is viewed by reflection measuring apparatus 94 through a length of coaxial cable 10, as well as through a length of transmission line 27. If actual impedance is the parameter being measured, the length of transmission line must be compensated for in known fashion. If the length of transmission line between the measuring device 94 and impedance being measured (antenna 15 in conjunction with the reflective metallization on a surface of balloon membrane 23) is other than a multiple of a half-wavelength at the frequency of operation, compensation must be made for the transmission line. For example, assuming that coaxial cable 10 and cable 27 of FIG. 1a have a characteristic impedance of 50 ohms, all resistances and reactances are divided by 50 in order to enter the normalized Smith chart of FIG. 6. A 50 ohm impedance of coaxial cable 10 is illustrated in FIG. 6 by the center of a Smith chart, designated 610. Capacitive reactances are on the left of the chart, and inductive reactances are on the right of the chart. Resistances lie on the central vertical axis of the chart, 0 resistance at the top and infinite resistance at the bottom. Around the periphery of the chart are numbers representing wavelengths measured in the intervening coaxial cable between the measuring device and the impedance being measured. Arrow 602 represents progress in the direction away from the impedance being measured and towards the measuring device. A dipole antenna near resonance has a resistive component of impedance near 70 ohms, which when normalized equals 1.4, corresponding to point 612 in FIG. 6. Antenna 15, due to the presence of metallization 98 on balloon membrane 23, may have a substantial capacitive reactance component, which may be increased if the antenna is longer than required for resonance. The reactive component of the antenna impedance might also represent 70 ohms, which is a normalized capacitive reactance of 1.4. Since the impedance of reactance point 614 is capacitive, it falls to the left of the chart, at a normalized capacitive reactance of 1.4. Point 614 lies on a radial 616 passing through the wavelength designation 0.31. Radial 616 is a reference line. Measurement of an impedance such as that represented by point 614 through a length of transmission line having a length $0.5-0.31=0.19$ wavelengths would show an impedance having zero reactance at a resistance value corresponding to a point 617, corresponding to a normalized resistance of 0.32, which in a 50 ohm system is about 16 ohms. As the length of line is increased beyond 0.19 wavelengths, the measured impedance would show a positive reactive component or inductive component, as the length of transmission line increases towards 0.44 wavelengths, both the resistive and reactive components grow bigger, until a normalized resistive value of 3.0 (corresponding to 150 ohms in a 50 ohm system) is reached. Further increases in the lengths of intervening transmission line once again introduce a capacitive component.

Figure 12:
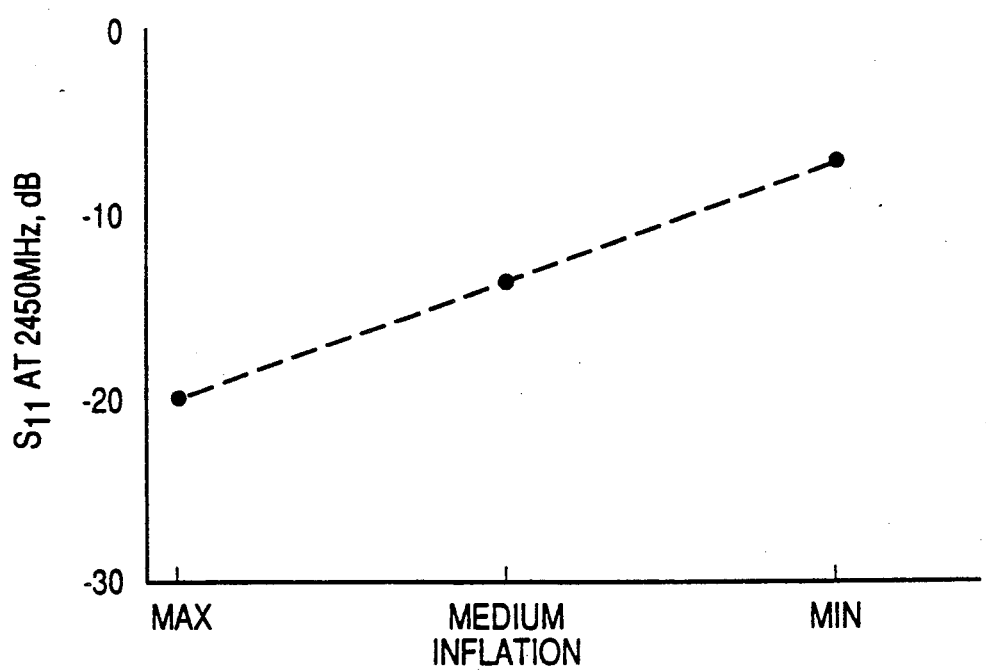
FIG. 12 is a plot of $S_{11}$ versus balloon inflation derived from the plot of FIG. 11.

If impedance is to be measured, the length of the transmission line in wavelengths must be accurately known. It has been found, however, that a different characteristic of impedance, namely reflection coefficient or $S_{11}$, can provide an adequate indication. FIG. 11 illustrates plots of reflection coefficient $S_{11}$, measured in dB, for a range of frequencies encompassing medical applications, of the impedance at the proximal end of a 50-ohm transmission line terminated at its distal end in a simple antenna, such as that of FIG. 1a, surrounded by a balloon having metallization similar to that illustrated in FIG. 8 and filled to different diameters with saline solution. In FIG. 11, the 910 MHz medical frequency is identified with an arrow 1110, and the 2450 MHz medical frequency is identified by an arrow 1112. The plot was made by an automatic impedance measuring system, a Hewlett-Packard 8510 network analyzer. Plot 1118 in FIG. 11 represents the superposition of a plurality of plots of a substantially fully inflated balloon to illustrate repeatability, plot 1116 represents a half-inflated balloon, and plot 1114 is a plot of a substantially deflated balloon. As can be seen, repeatability is excellent near the 2450 MHz frequency. The significance of the plot of FIG. 11 may be more readily appreciated by plotting S11 versus inflation, as in FIG. 12. As can be seen in FIG. 12, about 13*db* of change in the magnitude of S11 occurs between minimum and maximum inflation under the conditions of the test. It is noted that the test was conducted with the balloon in free space, and therefore the results are only indicative of change, and are not indicative of the actual magnitude of the change which can be expected in a human body, which must be determined for the particular balloon configuration, characteristics of the metallization pattern, molarity of the solution in the balloon, and the like.

In accordance with an aspect of the invention, a lossy fluid such as saline solution is used to inflate the balloon of the catheter. Those skilled in the art know that the saline solution is conductive and tends to absorb microwave radiation. However, in accordance with the invention, a dual heating modality is obtained by the use of saline solution within the balloon. The microwave signal applied to the proximal end of the catheter is transmitted down coaxial cable 10 towards the distal end and is radiated by antenna 15. A portion of the power radiated by the antenna is absorbed by the saline solution, and a portion of the power is transmitted through the saline solution for direct heating of the plaque. That portion of the power which is absorbed by the saline solution causes heating thereof, which provides direct conductive heating of the plaque by thermal conduction through membrane 23 of the balloon. Thus, the described catheter may be used in a dual mode, which includes direct microwave heating of plaque, together with conductive heating of plaque through intermediate heating of an electrically lossy fluid within the balloon. The same catheter can additionally be used in conjunction with microwave reflection measuring equipment such as impedance measuring equipment, $S_{11}$ measuring equipment or time-domain reflection measuring equipment for determining the distension of the balloon and therefore the diameter of the distended lumen.

Figure 13:
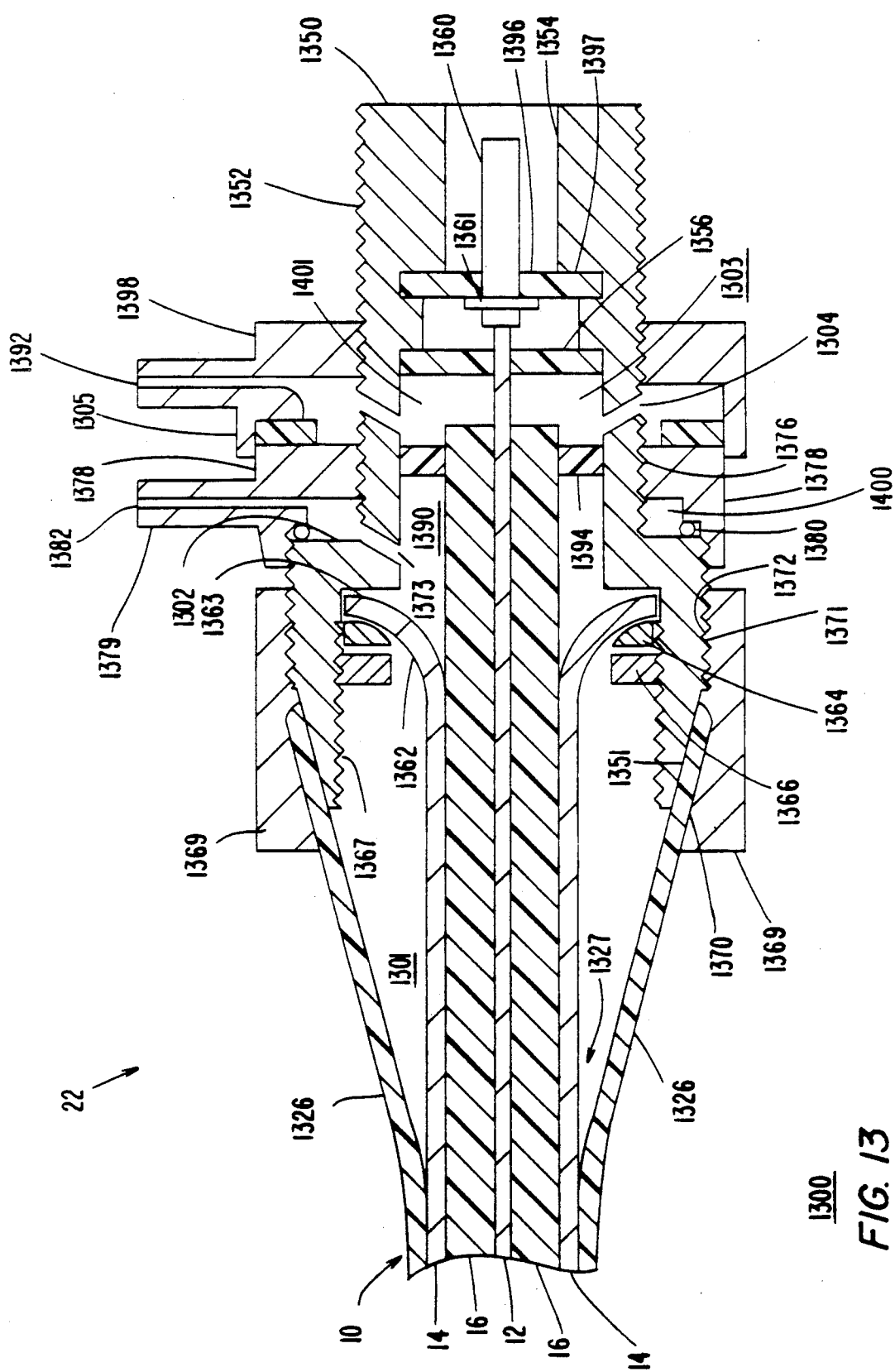
FIG. 13 illustrates in cross-section a connector which may be used to make electrical and fluid connections to a catheter in accordance with the invention.

In FIG. 13, a connector designated generally as 1300 provides a tight connection between a gas or liquid source and a channel 1327 lying between flexible jacket 1326 and braided outer conductor 14. Channel 1327 also includes interstices within braided outer conductor 14. Since a liquid cannot easily be forced through a single channel into the balloon at the distal end of a catheter without creating a bubble, it is advantageous to take advantage of the interstices in the braided center conductor of coaxial cable 10 to allow the escape of gas during filling of the balloon with liquid. Connector 1300 also provides an electromagnetic transmission-line path between a coaxial connector and the interior of coaxial cable 10. In FIG. 13, connector 1300 at proximal end 22 of catheter 8 includes a conductive housing 1350 including an externally threaded portion 1352 and a bore 1354. A first gas-impermeable dielectric washer 1396 bears against a shoulder 1397 of housing 1350. The junction between washer 1396 and shoulder 1397 may include a sealer to aid in preventing leakage of gas. If the interior of the connector is pressurized, washer 1396 is forced against shoulder 1397. A center conductor connector 1360 is slotted to receive a mating male center conductor (not illustrated) and includes a shoulder 1361 for bearing against the edge of an aperture in the center of washer 1396. The proximal end of center conductor 12 extends through the center of a dielectric washer 1356 and is soldered into a recess (not illustrated) in the end of pin 1360. Washer 1356 bears against a shoulder of housing 1350 to support center conductor 12 and to provide additional sealing between a chamber 1303 and washer 1396. A further dielectric washer 1394 makes a gas-tight fit against the outer surface of dielectric material 16, and its outer edge bears against a further shoulder of housing 1350 to define a second side of chamber 1303.

The proximal end of outer conductor 14 is unbraided and flared out to form a curve 1362 which fits against a curved shoulder 1363 of housing 1350. The outer conductor id captivated against shoulder 1363 by a washer or ring 1364 having a curvature matching that of shoulder 1363 and a ring-shaped screw 1366 having external threads which mate with an internally threaded portion 1367 of housing 1350. The connection of jacket 1326 to housing 1350 is accomplished by flaring the flexible jacket and slipping it over a tapered exterior portion 1351 of housing 1350. Jacket 1326 is captivated against surface 1351 by a nut 1369 having a tapered interior portion 1370 which matches the taper of portion 1351 of housing 1350. Nut 1369 has a threaded portion 1371 which engages with threads 1372 of housing 1350 so as to make a fluid tight seal between jacket 1326 and housing 1350. In order to introduce fluid into the interior of a chamber 1390 within connector 1300, a plurality of holes 1373 are drilled through the body of housing 1350 near the base of threaded portion 1352. An annular plenum housing 1378 including an interior threaded portion 1376 and a nipple 1382 is screwed over threaded portion 1352 of housing 1350, and compresses an O-ring 1380 against a shoulder 1302 of housing 1350 to define a plenum 1400. Thus, nipple 1382 communicates with plenum 1400 and, by way of drilled holes 1373, with a chamber 1390, which communicates through the unbraided strands of outer conductor 1362 to a further chamber 1301 defined in the conductive outer sheath, and between sheath 14 of coaxial cable 10 and flexible jacket 1326. Fluid may be introduced through bore 1382 of nipple 1379, and through chambers 1400, 1390 and 1301, and channel 1327 to the distal end of the coaxial cable. As fluid flows through channel 1327 towards the distal end of the catheter, displaced fluid (gas or liquid) may return through the interstices in braided center conductor 12, returning to chamber 1303 defined between washers 1394 and washer 1356. Chamber 1303 communicates through drilled holes 1304 with a plenum 1401 defined by plenum housing 1398, which is screwed over threaded portion 1352 of connector body 1350 and which bears against a washer 1305 for sealing. Fluid escaping through the center conductor passes through chamber 1303, holes 1304 and through a nipple 1392. Naturally, other arrangements are possible for making electromagnetic coaxial connections to coaxial cable 10 and fluid connections to fluid channel 1327 extending through cable 10, and to any additional fluid channels in cable 10, as through the interstices in the center conductor.

Figure 14:
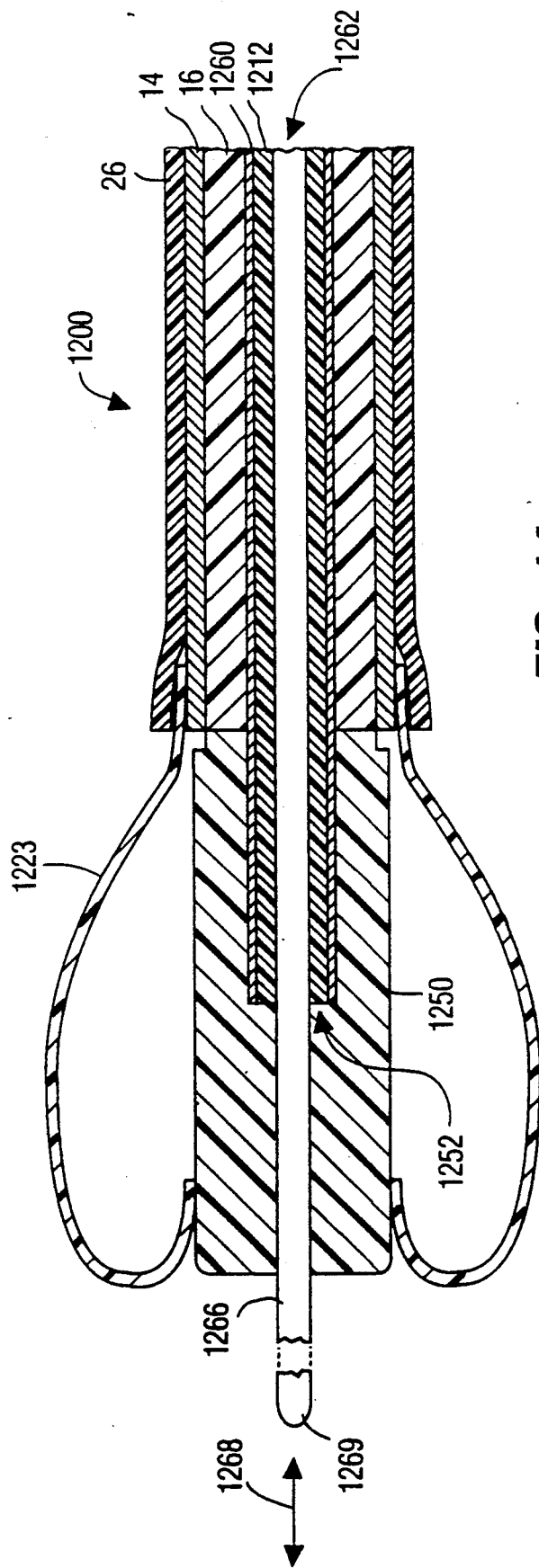
FIG. 14 illustrates in cross-section a catheter through which a guide wire or filament passes.

In FIG. 14, a coaxial transmission line 1200 includes a center conductor formed from a dielectric tube 1212 with a metallic exterior plating illustrated as 1260 and a central bore 1262. Dielectric tube 1212 may be made from a fluorocarbon material such as TEFLON (polytetrafluoroethylene) and metallization 1260 may be a gold plating. Transmission line 1200 also includes a dielectric sheath 16, an outer conductor 14, and a jacket 26, corresponding to those of FIG. 1. A dielectric piece 1250 accepts the center conductor 1212, 1260 in a large diameter portion of a bore 1252, and also includes a smaller diameter portion of bore 1252 which matches the diameter of bore 1262 of the center conductor. As in the arrangement of FIG. 1c, dielectric piece 1250 supports an os of a balloon 1223, illustrated in a partially inflated form. In accordance with an aspect of the invention, a guide filament is adapted to be disposed within bore 1252. The guide filament is longer than the center conductor bore so that the guide filament may simultaneously protrude from both the distal and proximal (not illustrated) ends. In FIG. 14, a catheter guide filament 1266 extends from the proximal end of the transmission line (not illustrated) to the distal end where its end 1269 protrudes. Filament 1266 is dimensioned to be longitudinally movable within the transmission line, in the directions illustrated by double-headed arrow 1268. The filament may be extended through and out of the distal end of transmission line 1200 in order to guide the catheter in known fashion.

The filament may be of conventional metallic construction. When balloon 1223 is inflated (with lossy fluid, if desired) and it is desired to apply microwave power through the transmission line, filament 1266 is partially withdrawn by motion toward the proximal end, thereby causing the end 1269 of the filament to be withdrawn to within the center conductor, where its effect on the antenna radiation is reduced. Alternatively, at least the end of filament 1266 which protrudes past the end of center conductor 1212, 1260 may be made from a dielectric material or a high-resistance material, so that its effect on the radiation is reduced even if it is not withdrawn during application of microwave power.

Other embodiments to the invention will be apparent to those skilled in the art. In particular, additional channels for the flow of fluid may be made by cutting longitudinal troughs part-way through the exterior portion of dielectric sheath 16. Lossy fluids other than saline solution may be used as required to obtain the correct dielectric constant, loss and physiological compatibility. Instead of using switches such as switch 30 of FIG. 1a, a directional coupler such as a 30 dB bidirectional coupler can be used to sample power for measuring apparatus 94.

What is claimed is:

1. A method for measuring the diameter of a vas or blood vessel at a particular point, comprising the steps of:
   obtaining access to the interior of said bas;
   inserting into said vas the distal end of an electromagnetic transmission line terminated at said distal end in an antenna surrounded by a deflated dielectric balloon carrying a conductive pattern;
   adjusting said antenna and deflated balloon to a position adjacent said point;
   said applying pressure for inflating said balloon;
   applying a radio frequency signal to the proximal end of said transmission line;
   measuring a characteristic of said signal attributable to reflections from said conductive pattern with said balloon pressurized for inflation against the walls of said vas; and
   establishing the diameter of said vas at said point from said characteristic of said signal.

2. A method according to claim 1 wherein said step of applying pressure comprises the step of inflating with a dielectric liquid.

3. A method according to claim 1 wherein said step of applying pressure comprises the step of inflating with a lossy dielectric liquid.

4. A method according to claim 1 wherein said step of measuring said characteristic of said signal comprises the step of measuring the return loss.

5. A method according to claim 1 wherein said step of measuring said characteristic of said signal comprises the step of measuring the impedance.

6. A method according to claim 1 wherein:
   said step of applying a radio frequency signal comprises the step of applying a step change in a characteristic of said radio frequency signal at a predetermined time; and
   measuring the interval between said predetermined time and the time at which said step change is reflected from said conductive pattern.

7. A catheter comprising:
   an elongated coaxial electromagnetic transmission line defining a distal end and also defining a proximal end adapted for receiving electromagnetic power at a predetermined frequency;
   antenna means coupled to said distal end of said transmission line for coupling electromagnetic power between said transmission line and a region about said antenna means at least at said predetermined frequency;
   balloon means physically attached to said transmission line near said distal end thereof, said balloon means surrounding said antenna means and being adapted for inflation; and
   electromagnetic reflection means resonant near said predetermined frequency, and mounted on said balloon means, for being positioned closer to and farther from said antenna means in response to deflation and inflation, respectively, of said balloon means.

8. A catheter according to claim 7 wherein said coaxial transmission line comprises:
   an elongated center conductor extending from said distal end to said proximal end of said transmission line; and
   an elongated outer conductor surrounding and spaced away from said center conductor from said distal to said proximal end of said transmission line.

9. A catheter according to claim 8 wherein said antenna means comprises:
   an extension of said center conductor distally of the distal end of said outer conductor.

10. A catheter according to claim 9 wherein said reflection means comprises:
    elongated conductive means mounted on said balloon means.

11. A catheter according to claim 10, wherein said elongated conductor means is conductively isolated from said transmission line.

* * * * *